US012383382B2

(12) United States Patent
Kuo

(10) Patent No.: US 12,383,382 B2
(45) Date of Patent: Aug. 12, 2025

(54) METHODS FOR TRACKING ORTHODONTIC TREATMENT PROGRESS

(71) Applicant: Align Technology, Inc., San Jose, CA (US)

(72) Inventor: Eric Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 166 days.

(21) Appl. No.: 17/444,037

(22) Filed: Jul. 29, 2021

(65) Prior Publication Data

US 2021/0378799 A1    Dec. 9, 2021

Related U.S. Application Data

(60) Continuation of application No. 16/136,625, filed on Sep. 20, 2018, now abandoned, which is a division of application No. 13/719,823, filed on Dec. 19, 2012, now Pat. No. 10,098,714.

(51) Int. Cl.

| | |
|---|---|
| *A61C 9/00* | (2006.01) |
| *A61C 7/00* | (2006.01) |
| *A61C 7/02* | (2006.01) |
| *A61C 13/12* | (2006.01) |
| *A61C 13/34* | (2006.01) |
| *A61C 19/04* | (2006.01) |

(52) U.S. Cl.
CPC .............. *A61C 9/006* (2013.01); *A61C 7/002* (2013.01); *A61C 7/02* (2013.01); *A61C 9/0093* (2013.01); *A61C 13/12* (2013.01); *A61C 13/34* (2013.01); *A61C 19/04* (2013.01)

(58) Field of Classification Search
CPC ....... A61C 9/006; A61C 9/0093; A61C 7/002; A61C 7/02; A61C 13/12; A61C 13/34; A61C 19/04
See application file for complete search history.

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |

(Continued)

*Primary Examiner* — Nicholas D Lucchesi
*Assistant Examiner* — Hao D Mai
(74) *Attorney, Agent, or Firm* — FORTEM IP LLP

(57) ABSTRACT

Methods for tracking progress of a patient undergoing orthodontic treatment are provided. In some embodiments, a method includes receiving a 3D model of a dental arch. The 3D model can be generated by receiving a plurality of images of the dental arch, at least some of the images including a portion of the dental arch together with a portion of a reference element. A registration can be determined between an image and at least one other image using the portions of the reference element in the respective images to improve registration accuracy. The plurality of images can be stitched together according to the determined registrations to generate the 3D model of the dental arch. The method can further include assessing progress of the orthodontic treatment by comparing the 3D model of the dental arch to a previous 3D model representing an earlier state of the dental arch.

21 Claims, 6 Drawing Sheets

(56) References Cited

U.S. PATENT DOCUMENTS

| | | |
|---|---|---|
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,198,627 B2 | 12/2015 | Suttin et al. |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 2002/0102517 A1* | 8/2002 | Poirier .................. A61C 1/084 433/213 |
| 2006/0212260 A1* | 9/2006 | Kopelman ............. G16H 50/50 702/152 |
| 2007/0003900 A1* | 1/2007 | Miller ...................... A61C 7/00 433/24 |
| 2008/0286715 A1* | 11/2008 | Choi ................... A61C 19/055 901/44 |
| 2008/0305451 A1* | 12/2008 | Kitching ................ A61C 7/002 433/24 |
| 2008/0306724 A1* | 12/2008 | Kitching .................. A61C 7/00 704/2 |
| 2014/0170587 A1* | 6/2014 | Kopelman ....... A61B 1/000095 433/29 |
| 2019/0029784 A1 | 1/2019 | Moalem et al. |
| 2019/0388193 A1 | 12/2019 | Saphier et al. |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349698 A1 | 11/2020 | Minchenkov et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0113308 A1 | 4/2021 | Jo et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |

\* cited by examiner

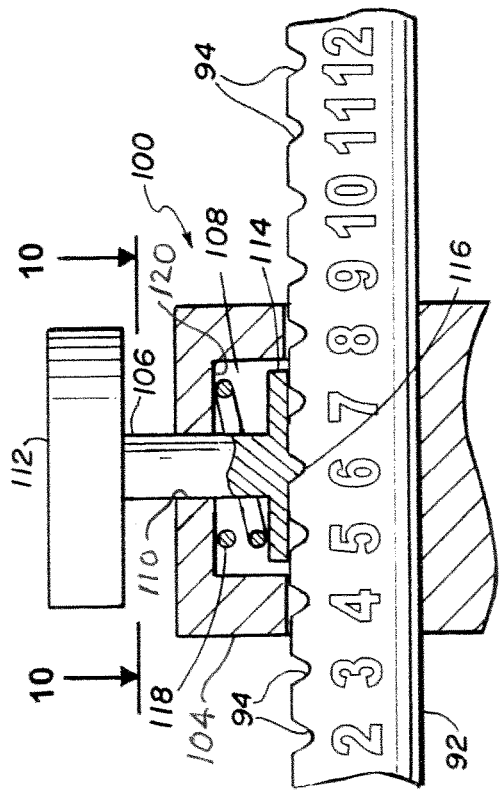
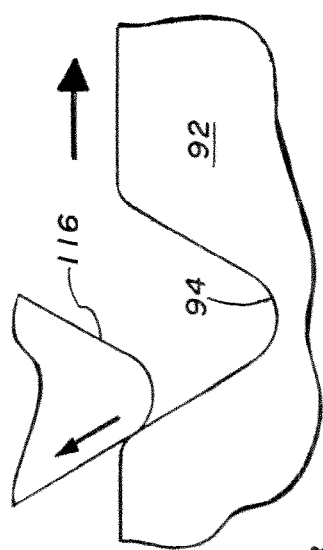
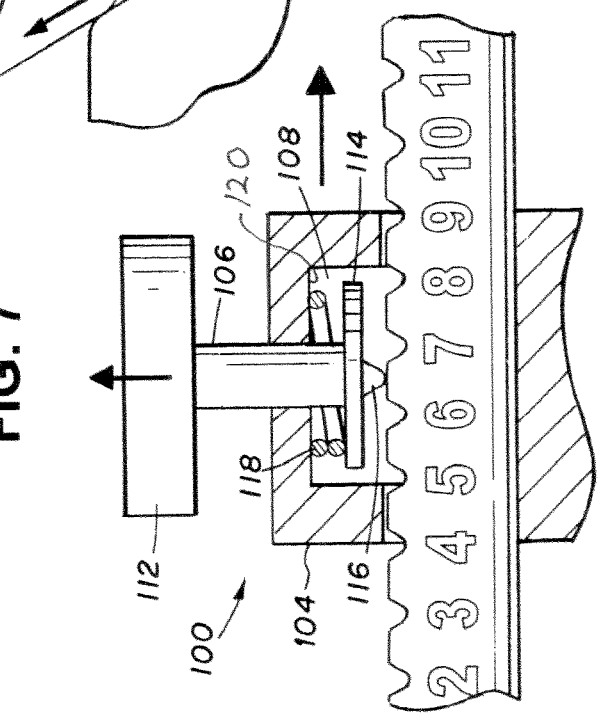
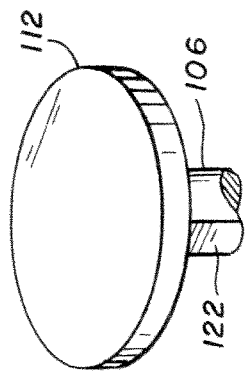
FIG. 7
FIG. 9
FIG. 8
FIG. 10
FIG. 11

METHODS FOR TRACKING ORTHODONTIC TREATMENT PROGRESS

CROSS-REFERENCE TO RELATED APPLICATIONS

This application is a continuation application of U.S. patent application Ser. No. 16/136,625, filed Sep. 20, 2018, which is a divisional application of U.S. patent application Ser. No. 13/719,823, filed Dec. 19, 2012, now U.S. Pat. No. 10,098,714, the disclosures of each of which are incorporated herein by reference in their entireties.

FEDERALLY-SPONSORED RESEARCH OR DEVELOPMENT

Not Applicable

BACKGROUND

This disclosure relates generally to the field of optical scanners. More specifically, the disclosure relates to a system, method, and apparatus for accurately and repeatably scanning an object with a scanner, such as an optical scanner, wherein an object to be scanned is fixed positionally relative to a reference pattern.

In a specific embodiment, a system, method, and apparatus in accordance with this disclosure relates to intra-oral scanning of a patient's dentition in connection with the prosthodontic and orthodontic treatment of dental conditions such as mal-alignment of dentition and the replacement of missing teeth. In accordance with this embodiment, this disclosure relates to an apparatus, system, and method for intra-oral scanning of a patient's dentition for providing a course of treatment for such conditions, and, in a specific embodiment, for providing a series of appliances that would implement the course of treatment.

Optical scanning of a three-dimensional object typically involves the use of an optical scanner that obtains and renders a digitized 3-D image of the object. The typical optical scanner employs a scanner head that takes a series of individual 3-D images of predetermined segments of the object, segment-by-segment, in either a predetermined or user-directed sequence. The scanner employs software that digitizes the segment images and then "stitches" them together to render a composite 3-D image of the entire object (or at least the portion of the object for which a composite image is desired). Thus, in cases where the object is larger than a single segment image, multiple segment images are required to render the desired composite image.

A problem may arise, however, in cases where the object has one or more "smooth" surfaces, i.e., surfaces having few, if any, distinctive features, or surfaces having gradual (non-abrupt) shape transitions. In such situations, each segment image may fit along a large number of orientations relative to an actual desired placement or position within the object as a whole. In other words, if the entire object is considered to be a completed mosaic made of individual segment images, each segment image may be likened to an individual mosaic piece. Where the completed mosaic is relatively featureless, it may be difficult, if not impossible, to determine exactly where, in the completed mosaic, each individual piece is located and how it is oriented with respect to other mosaic pieces. Therefore, it would be desirable to provide some way to provide a reference pattern that may be scanned along with the object, so that each segment image will include a corresponding reference image that provides a fixed registration for the segment image for determining a location and orientation for the segment image relative to the other segment images that constitute the desired composite image.

One specific application of optical scanning is intra-oral scanning of a patient's dentition. Intra-oral scanning typically involves the use of an optical scanner that obtains a digitized 3-D image of a patient's dentition without the need for making a physical model, such as a casting or "stone" of an impression of a patient's dental arch. While dental arches typically have sufficient surface features to avoid (or at least to minimize to a manageable degree) the above-noted problems with relatively featureless objects, the use of a registration mechanism to provide a segment image that includes a reference image would likely result in faster image-generation speeds with respect to the rendering of a computer-generated composite image of the entire dental arch. Moreover, there are cases, such as scanning an edentulous (toothless) arch (for, e.g., the fitting of dentures), in which the problems of scanning a relatively featureless object may be present to varying degrees. Furthermore, in creating a treatment plan or course of treatment for a prosthodontic or orthodontic treatment of a patient, it is typically necessary or desirable to take an intra-oral scan of one or both of the patient's dental arches before beginning the treatment plan, and then to take one or more subsequent scans at various stages during the course of treatment, or at least after the course of treatment has been completed. In such cases, it would be desirable to assure that the pre-treatment scan and all subsequent treatment scans are taken with respect to the same fixed reference frame, so that the position of the dentition in the scanned dental arch at a time $T_N$ may quickly and accurately be determined relative to the position of the dentition at an earlier time, for example a pre-treatment time $T_0$.

SUMMARY

In accordance with a first aspect of this disclosure, there is provided a method for intra-orally scanning at least a portion of a dental arch of a patient, the method comprising providing a reference element having a reference pattern thereon; installing the reference element inside the oral cavity of a patient in a fixed position adjacent to and spaced from the dental arch; holding the reference element in the fixed position without contacting an occlusal surface of the dental arch; and intra-orally scanning at least a portion of the dental arch and an adjacent portion of the reference element to obtain a scanned image comprising the scanned portion of the dental arch and the scanned adjacent portion of the reference pattern.

In accordance with a second aspect of this disclosure, there is provided a system for intra-orally scanning at least a portion of a dental arch of a patient, the system comprising a reference element having a reference pattern thereon; a reference element holding mechanism configured to hold the reference element in a fixed position inside the oral cavity of the patient adjacent to and spaced from the dental arch, wherein the reference element holding mechanism is configured to be installed on the patient without contacting an occlusal surface of the dental arch; and an intra-oral scanner configured to scan at least a portion of the dental arch and an adjacent portion of the reference element to obtain a scanned image comprising the scanned portion of the dental arch and the scanned adjacent portion of the reference pattern.

In accordance with a third aspect of this disclosure, there is provided a system for scanning an object, comprising: an object holding device including a reference pattern thereon, the object holding device being configured to hold an object adjacent to and spaced from the reference pattern; and a scanner configured to scan the object and the reference pattern simultaneously so as to obtain a scanned image of the object with the reference pattern.

In accordance with a fourth aspect of this disclosure, there is provided a method of scanning an object, comprising: holding the object in a fixed location adjacent to and spaced from a reference pattern; and scanning the object and the reference pattern simultaneously so as to obtain a scanned image of at least a first portion of the object with at least a first portion of the reference pattern.

In accordance with a fifth aspect of this disclosure, a system for ascertaining the progress of a course of orthodontic and/or prosthodontic treatment of the dentition of a patient, the system comprising a reference element having a reference pattern thereon; a holding device configured to hold the reference element at a fixed position adjacent to and spaced from a portion of the dentition of the patient designated for the treatment without contacting an occlusal surface of the dentition, the fixed position corresponding to a set of position settings for the holding device; an input device configured to receive input representing the set of position settings; an intra-oral scanner configured to scan the portion of the patient's dentition simultaneously with an adjacent portion of the reference element to obtain a scanned image comprising the scanned portion of the dentition and a scanned portion of the reference pattern on the adjacent portion of the reference element; a converter configured to create a digitized representation of the scanned image; a processor, operatively associated with the input device, configured to create an input data set that represents the position settings and to match the input data set with the digitized representation of the scanned image to produce a combined data file that includes the digitized representation of the scanned image and the data representing the position settings.

BRIEF DESCRIPTION OF THE DRAWINGS

FIG. 4 is a cross-sectional view taken along line 4-4 of FIG. 1;

FIG. 5 is cross-sectional view taken along line 5-5 of FIG. 1;

FIG. 7 is a partial cross-sectional view of the incremental position adjustment element shown in FIG. 6, showing the element in a selected incremental position;

FIG. 8 is a view similar to that of FIG. 7, but showing the incremental position adjustment element in the process of being adjusted to another incremental position;

FIG. 9 is a detailed view of a first portion of the position adjustment element shown in FIGS. 6-8;

FIG. 10 is a cross-sectional view taken along line 10-10 of FIG. 9;

FIG. 11 is a detailed perspective view of a second portion of the position adjustment element shown in FIGS. 6-10;

DETAILED DESCRIPTION

Figure 1:
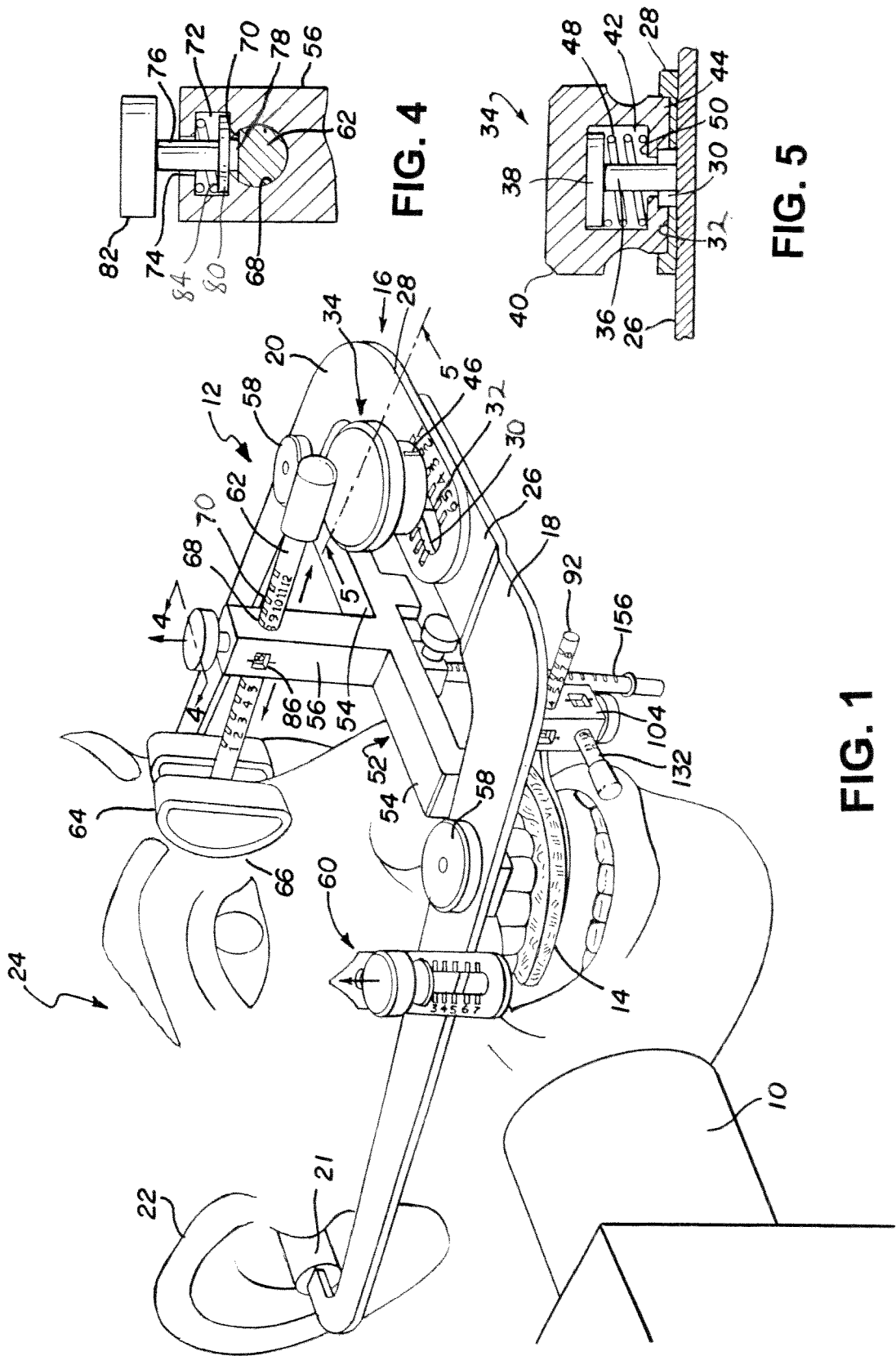
FIG. 1 is a perspective view of an apparatus for scanning a patient's dental arch in registration with a reference pattern, in accordance with an aspect of the disclosure.

Referring to the drawings, an exemplary apparatus for optically scanning an object in registration with a reference pattern, in accordance with an embodiment of the disclosure, may now be described. Referring to FIG. 1, the apparatus includes an optical scanner 10, advantageously an intra-oral scanner of a type well-known in the art. The scanner 10 is represented schematically only, and the drawing is in no way limiting with respect to this feature. The apparatus in accordance with this embodiment also includes a reference element fixation device 12 to which a reference element 14 is attached in a position-adjustable manner, as will be described below. In accordance with an exemplary embodiment, the fixation device 12 may be in the form of a head brace, similar to commercially available head braces used with intra-oral scanning systems. One such head brace is the "Panamount Face Bow," marketed by Panadent Corporation, of Grand Terrace, CA, USA. As will be described below, the fixation device 12, if embodied as a head brace, includes significant modifications that differentiate it from commercially available head braces, such as the "Panamount Face Bow." For example, as described below, the head brace used in the present disclosure is adjustable only in discrete measured increments, and not continuously adjustable, as is a conventional head brace of the "Face Bow" type. Furthermore, the head brace-type fixation device 12 of the present disclosure lacks a "bite plate" configured to be inserted between the dental arches of the patient and to be "clamped" between the upper and lower dental arches. In fact, preferably, no part of the fixation device contacts the teeth of the patient, or at least the occlusal surfaces of the teeth.

In a broader aspect, however, the fixation device 12 may be any device that holds the reference element 14 and allows it to be installed in the oral cavity of a patient in a reproducible fixed position relative to a dental arch of the patient, wherein the reproducible fixed position is obtained by adjusting the fixation device 12 in discrete measured increments until the reference element 14 is in the desired reproducible fixed position with respect to the dental arch to be scanned in registration with the reference element.

In accordance with the illustrated exemplary embodiment, the fixation device 12 includes a generally-U-shaped lateral positioning element or nasion relator 16, comprising first and second bracing arms 18, 20. The first arm 18 extends from a proximal end portion 21 configured to be inserted into the outer ear canal of one of the ears 22 of a patient 24, to a distal portion 26 that bends in front of the face of the patient 24. Similarly, the second arm 20 extends from a proximal end portion (not show) that is configured for insertion into the outer ear canal of the other ear (not shown) of the patient 24, to a distal portion 28 that overlaps the distal portion 26 of the first arm 18. The distal portion 28 of the second arm 20 is provided with a slot 30 extending laterally with respect to the patient's face, with a plurality of notches 32 extending from one or both sides of the slot 30 at discrete measured intervals. Advantageously, the distal portion 28 of the second arm 20 is provided with numerical markings adjacent each notch 32 on at least one side of the slot 30. Each notch 32 (or opposed pair of notches 32) provides a position detent for a nasion relator adjustment mechanism as described below.

The distal portions 26, 28 of the arms 18, 20, respectively, are adjustably connected to each other by a nasion relator adjustment mechanism that is shown in FIGS. 1 and 5. As will be appreciated from the ensuing description, the nasion relator adjustment mechanism of the exemplary embodiment, along with the other position adjustment mechanisms of the exemplary embodiment (as will be described below), provides for positional adjustment of the head brace in all aspects relative to the dental arch to be scanned in discrete, measured increments, rather than the continuous adjustment provided by the commercially available devices. The significance of this improvement will be made clear below.

Referring again to FIGS. 1 and 5, the nasion relator adjustment mechanism includes the overlapping distal portions 26, 28 of the arms 18, 20, respectively, and a nasion relator position locking device 34. The nasion relator position locking device 34, in one embodiment, includes a pin 36 (FIG. 5) extending upward from the distal portion 26 of the first arm 18 through the slot 30 in the distal portion 28 of the second arm 20 and terminating in a flat head 38, and a hollow adjustment knob 40 defining a cavity 42 that receives the pin 36, with the head 38 of the pin 36 engaging the top of the cavity 42. The lower end of the knob 40 has a protrusion or tooth 44 that is configured to seat within the notches 32. Advantageously, the knob 40 may also be provided with a marker or indicator 46 (FIG. 1) that provides a visual indication of the specific numbered detent notch 32 in which the knob tooth 44 is seated. The knob cavity 42 also houses a coil spring 48 concentrically surrounding the pin 36 and captured between the head 38 of the pin 36 and a concentric spring seat 50, so as to bias the knob 40 toward the distal portion 28 of the second arm 20. When the knob tooth 44 is engaged with a selected detent notch 32, the distal portions 26, 28 of the arms 18, 20, respectively, are fixed or locked relative to each other in a position indicated by the number of the selected notch, as visually indicated by the knob marker 46. When the knob 40 is lifted vertically against the bias of the spring 48, the knob tooth 44 is disengaged from the previously-selected notch 32, and the distal portions 26, 28 of the arms 18, 20, respectively can be moved to a new relative position associated with a newly-selected notch 32.

As shown in FIG. 1, the nasion relator arms 18, 20 are pivotally attached to a transverse structure 52. The transverse structure 52 has first and second opposed horizontal support arms 54 extending from a vertical support member 56. Each of the support arms 54 terminates in a hinge 58 that pivotally connects one of the nasion relator arms 18, 20 to the transverse structure 52, thereby allowing the relative positions of the distal portions 26, 28 of the arms 18, 20, respectively, to be adjusted as described above. An adjustable orbitale pointer 60 may optionally be provided on one of the nasion relator arms (e.g., the first arm 18), as shown in FIG. 1, to provide a greater degree of planar accuracy, as is known in the art. If included, the orbitale pointer 60 may advantageously be positionally adjustable in discrete, measured increments by a detented position adjustment mechanism similar to that described above with reference to FIG. 5.

Referring to FIGS. 1 and 4, the fixation device 12 includes a face engagement mechanism configured to engage a portion of the face above the patient's oral cavity. In the illustrated exemplary embodiment, the face engagement mechanism, which includes a nasion pad stabilizer arm 62 terminating in a nasion pad 64, is supported in the vertical support member 56 of the transverse structure 52. The stabilizer arm 62 is positionally adjustable, forward and backward with respect to the patient's face, within the vertical support member, to assure that the nasion pad 64 engages the nasion region 66 (i.e., the bridge of the nose) of the patient when the fixation device 12 is installed, to provide greater stability for the fixation device 12 relative to the dental arch to be scanned. The stabilizer arm 62 is journaled in a bore 68 through the upper portion of the vertical support member 56. The stabilizer arm 62 is advantageously provided with a series of notches or depressions 70 along the length of its upward-facing surface, which notches or depressions provide detents demarking discrete positions that are spaced apart at measured intervals. The detent-forming notches 70 may advantageously be marked by numerals on one side of the arm 62. The upper end of the vertical support member 56 has a cavity 72 defined by a top wall with a first aperture 74 configured to receive a rod or pin 76. The lower end of the rod or pin 76 terminates in protrusion or tooth 78, just above which is an annular spring seat 80. The upper end of the rod or pin 76, which extends to the exterior of the vertical support member 56 through the aperture 74, terminates in an enlarged diameter gripping head 82. A coil spring 84 is installed concentrically around the rod or pin 76, and is seated between the spring seat 80 and the top wall of the cavity 72. The spring 84 biases the rod or pin 76 downward toward the stabilizer arm 62. Thus, the rod or pin 76 may be lifted vertically against the force of the spring 84 by the gripping head 82, to disengage the tooth 78 from a first notch or depression 70 on the stabilizer arm 62, allowing the stabilizer arm 62 to be moved forward or backward relative to the vertical support member 56, thus ensuring that the pad is firmly seated against the patient's nasion region 66. When a suitable position for the stabilizer rod 62 is found, the gripping head 82 is released, and the spring 84 forces the tooth 78 into engagement with the newly-selected notch or depression 70. In this manner, the position of the stabilizer arm 62 may be adjusted in discrete measure increments. To assist in observing which numbered notch or depression 70 has been selected, a window 86 may be provided in the side of the vertical support member 56 adjacent the bore 68, so as to allow the number associated with the selected notch or depression 70 to be seen.

Figure 2:
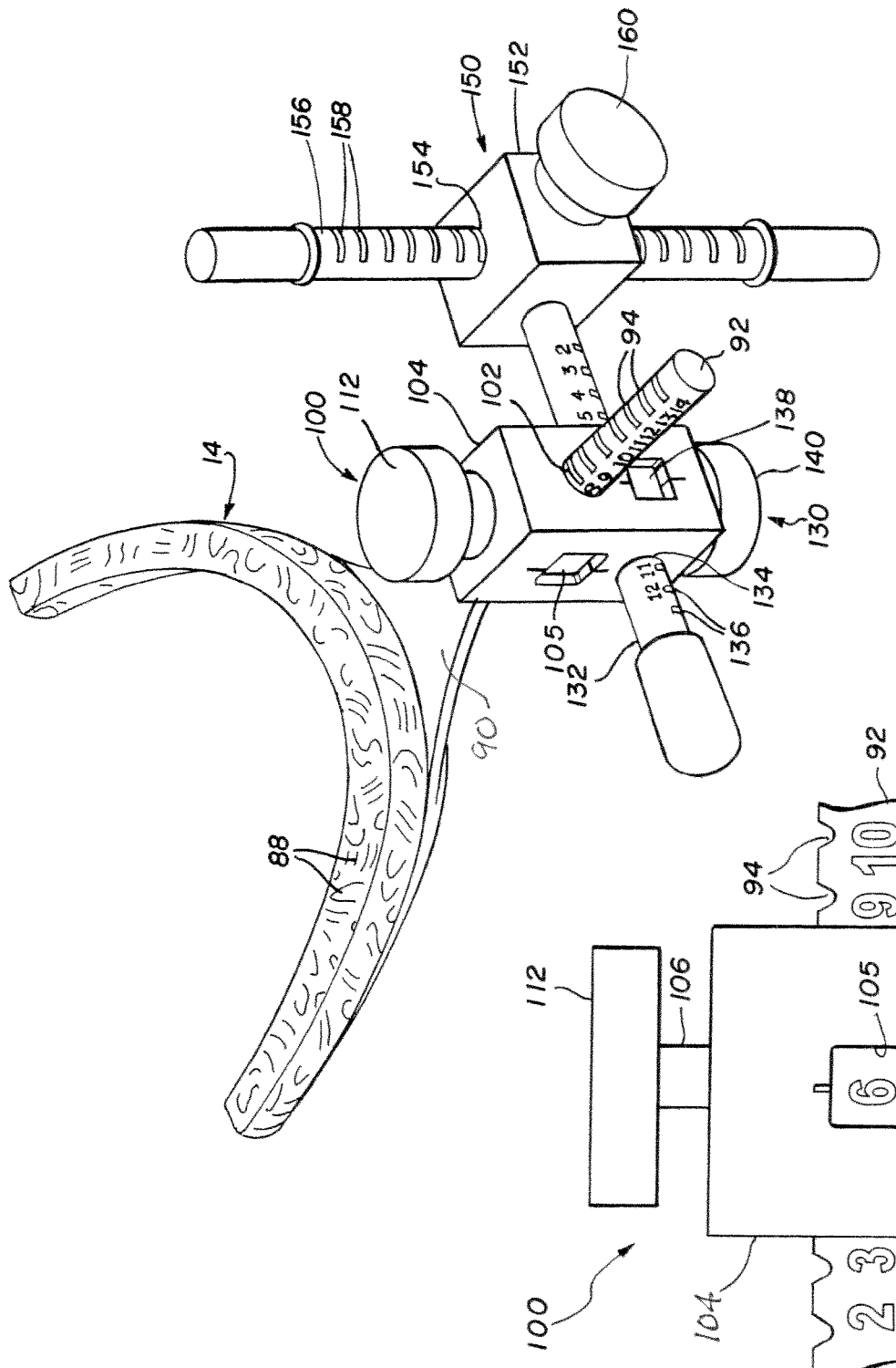
FIG. 2 is a detailed perspective view of a portion of the apparatus of FIG. 1, showing the reference element employed in an embodiment of the disclosure.
Figure 6:
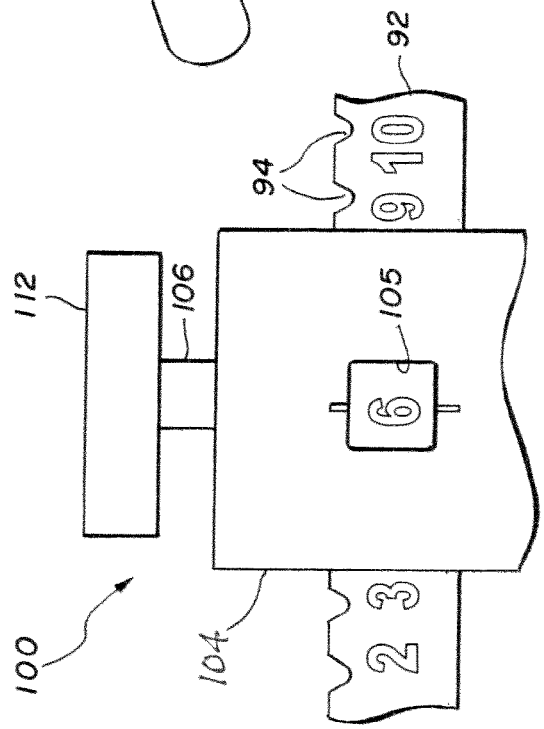
FIG. 6 is a detailed elevational view of an incremental position adjustment element of the apparatus of FIG. 1.

FIGS. 2, 3, and 6-11 show the reference element 14 and the arrangement for mounting it to the fixation device 12. Referring first to FIG. 2, the reference element 14 is shown as having a reference pattern 88 on its surface. The reference pattern 88, the purpose of which will be described below, is preferably three-dimensional; that is, it will have aspects that are defined by an X-Y-Z coordinate system relative to the surface of the reference element 14. In some embodiments, the reference pattern 88 may be only two-dimensional; that is, no aspects of it will extend out of the plane defined by a surface of the reference element 14. In embodiments in which the object to be scanned is a dental arch, the reference element 14 is advantageously in the configuration of a dental arch. The reference element 14 in such embodiments may be selected for a size and shape appropriate to a particular patient.

The reference element 14 is attached to a proximal end of a paddle 90, the distal portion of which is formed as a first adjustment rod 92 having a series of detent-forming notches or depressions 94 along the length of its upward-facing surface, which notches or depressions 94 define detents that are spaced apart at measured intervals. The notches or depressions 94 may advantageously be marked by numerals on one side of the first adjustment rod 92, as shown, for example, in FIG. 6. The first adjustment rod 92, which forms a part of a first reference element adjustment mechanism 100 (FIGS. 6-11), is journaled though a first bore 102 in a first adjustment mechanism housing 104 having a first window 105 through which the number of a selected notch or depression 94 can be observed. The position of the first adjustment rod 92 can be incrementally adjusted forward and backward relative to the patient the first reference element adjustment mechanism 100, which allows the selective engagement of any of the notches or depressions 94 as the rod 92 is displaced relative to the housing 104.

More specifically, as shown in FIGS. 6-11, the first reference element adjustment mechanism 100 includes a first position selection pin 106 situated in a cavity 108 defined in the housing 104 so as to communicate with the bore 102. The upper part of the selection pin 106 extends through an aperture 110 in the housing 104 orthogonal to the bore 102. The upper part of the pin 106 terminates in an enlarged-diameter gripping head 112. The lower part of the pin 106 includes an annular spring seat 114, from the center of which extends a ridge or tooth 116 that is positioned for engagement with the rod 92, and, more specifically, for seating in the notches 94. A coil spring 118, installed concentrically around the pin 106, is seated between the spring seat 114 and an upper housing wall 120 defining the cavity 108. The spring 118 biases the pin 106 inward in the housing 104, toward the rod 92. As shown in FIG. 10, the pin 106 may advantageously include a flat 122 that seats against a corresponding flat 124 in the aperture 110, to prevent the pin 106 from being rotated from its desired orientation.

As shown in FIGS. 7-9, the first reference element adjustment mechanism 100 allows the position of the first adjustment rod 92 to be selected by manipulating the position selection pin 106, via the gripping head 112, to disengage the tooth or ridge 116 of the pin 106 from a first notch 94 in the rod 92, thereby allowing the rod 92 to be moved relative to the housing 104, and to fix the rod 92 positionally relative to the housing 104 at a selected incremental position defined by another of the notches 94. In the illustrated embodiment, the first reference element adjustment mechanism 100 may be employed to adjust the position of the reference element 14 in discrete measured increments forward and backward relative to the dental arch to be scanned.

The lateral position of the reference element 14 relative to the dental arch to be scanned may be adjusted in discrete measured increments by a second reference element adjustment mechanism 130 (FIG. 2) that is similar in all material aspects to the first reference element adjustment mechanism 100. More specifically, in the illustrated exemplary embodiment, the second reference element adjustment mechanism 130 includes a second adjustment rod 132 journaled in a second bore 134 in the housing 104, the second bore preferably being orthogonal to the first bore 102. The second adjustment rod 132 is similar to the first adjustment rod 92. Thus, like the first adjustment rod 92, the second adjustment rod 132 has a series of notches or depressions 136 along the length of a downward-facing surface, which notches or depressions define detents that are spaced apart at measured intervals. The notches or depressions 136 may advantageously be marked by numerals on one side of the second adjustment rod 132. The housing 104 has a second window 138 through which the number of a selected notch or depression 136 can be observed. The position of the second adjustment rod 132 can be changed and selected relative to the housing 104 by a second spring-loaded position selection pin 140, structurally and functionally similar to the first position selection pin 106, as described above and as illustrated in FIGS. 6-11. Thus, manipulation of the second position selection pin 140 allows the selective engagement of any of the notches or depressions 136 on the second adjustment rod 132 as the latter is moved relative to the housing 104. Similarly to the forward and backward positional adjustment provided by the above-described first reference element adjustment mechanism 100, the lateral position of the reference element 14 relative to the dental arch to be scanned may be selected by manipulating the second position selection pin 140 to disengage it from a first notch 136 on the second adjustment rod 132 to allow the second adjustment rod 132 to be moved laterally relative to the first housing 104, and to fix the rod 132 positionally relative to the housing 104 at a selected incremental position. In the illustrated embodiment, the second reference element adjustment mechanism 130 may be employed to adjust the position of the reference element 14 laterally in discrete measured increments relative to the dental arch to be scanned.

The second adjustment rod 132 has one end that may advantageously be attached to a third position adjustment mechanism 150 (FIG. 2) that may be used to adjust the position of the reference element 14 vertically, in discrete, measured, incremental positions, with respect to the dental arch to be scanned. The third position adjustment mechanism 150 includes a second housing 152 having a vertical bore 154 therethrough, through which is journaled a third adjustment rod 156 that has an upper end fixed to the bottom of the transverse member 52 (see FIG. 1). Like the above-described first and second adjustment rods, the third adjustment rod 156 has a series of notches or depressions 158 along its length, which notches or depressions define detents that are spaced apart at measured intervals. The notches or depressions 158 may advantageously be marked by numerals on one side of the third adjustment rod 156. The second housing 152 may advantageously have a window (not shown) through which the number associated with a selected notch or depression 158 can be observed.

The position of the third adjustment rod 156 can be changed and selected relative to the second housing 152 by a third spring-loaded position selection pin 160, structurally and functionally similar to the first position selection pin 106, as described above and as illustrated in FIGS. 6-11.

Thus, manipulation of the third position selection pin 160 allows the selective engagement of any of the notches or depressions 158 on the third adjustment rod 156 as the latter is moved relative to the second housing 152. As in the above-described first reference element adjustment mechanism 100, the vertical position of the reference element 14 relative to the dental arch to be scanned may be selected by manipulating the third position selection pin 160 to disengage it from a first notch 158 on the third adjustment rod 156 to allow the third adjustment rod 156 to be moved vertically relative to the second housing 152, and to fix the third rod 156 positionally relative to the second housing 152 at a selected incremental position. As shown, in the illustrated embodiment, the third reference element adjustment mechanism 150 may be employed to adjust the position of the reference element 14 vertically in discrete measured increments relative to the dental arch to be scanned.

Figure 3:
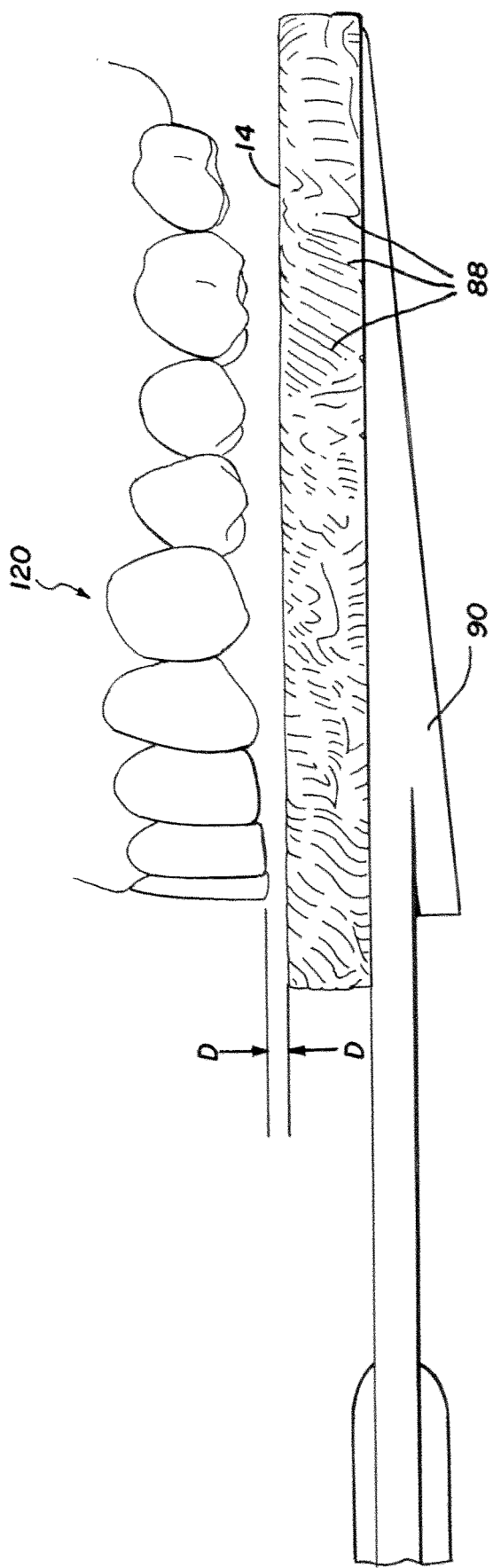
FIG. 3 is a side elevational view of the reference element shown in FIG. 2.

Referring to FIG. 3, the reference element 14 is shown as being located relative to a patient's upper dental arch 120 in a position that is appropriate for scanning the dental arch 120 together with at least an adjacent portion of the reference element 14. Note that, unlike conventional head brace devices, such as a "Face Bow," which employ a bite plate designed to be in contact with the teeth in the dental arch, the reference element 14 is separated from the dental arch 120 to be scanned by a known separation distance D. The value of D may be determined on a case-by case basis, or it may be predetermined for a preset range of dental arch sizes and configurations. Although the reference element 14 is shown positioned with respect to an upper dental arch, the same positional considerations would apply when the reference element is used for scanning a lower dental arch.

Because the reference element 14 does not need to contact the teeth, and is instead maintained at a predetermined distance from the teeth, all of the position settings of the position adjustment mechanisms described above are fixed for any given patient, and are thus easily reproducible for subsequent scans. Furthermore, depending on which arch is being scanned, and the angle from which the scan is taken, the reference element 14 can be configured for placement above the teeth of the upper arch, below the teeth of the lower arch, or directly in front of the teeth. In all cases, because the fixation device 12 holds the reference element 14 in a fixed position relative to the dental arch without contacting any occlusal surfaces of the patient's teeth, no part of the occlusal surfaces is obscured, thereby allowing all surfaces of the teeth to be scanned.

Figure 12:
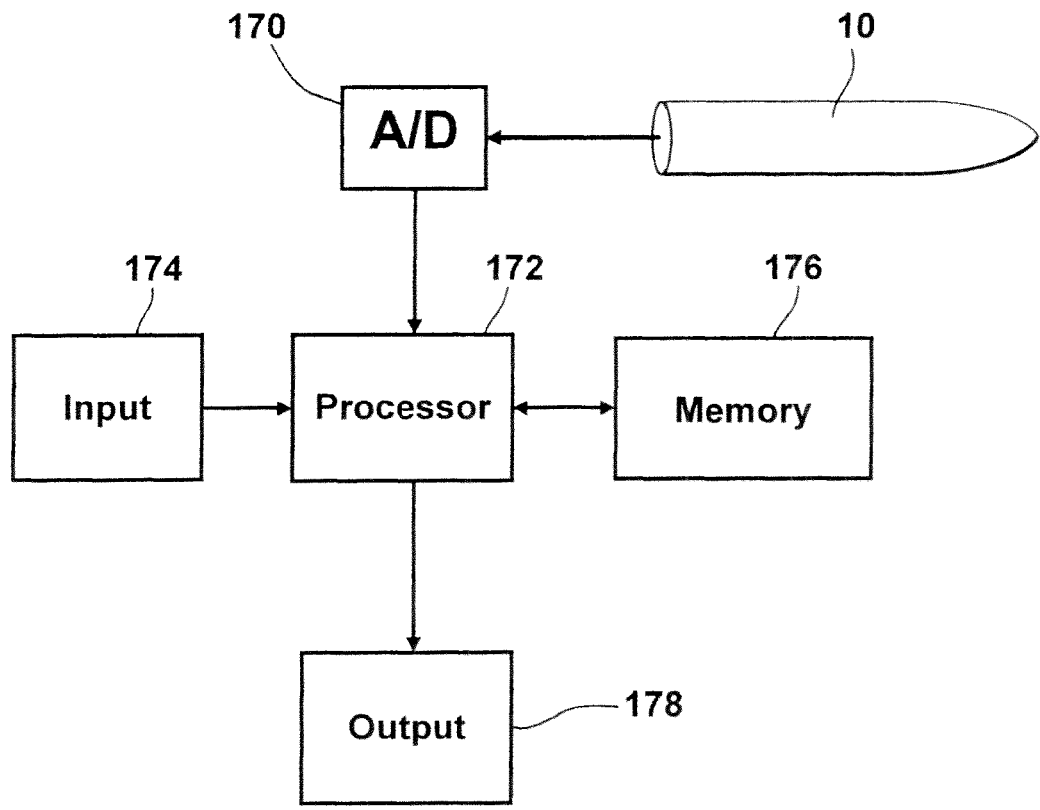
FIG. 12 is a diagrammatic representation of a scanning system in accordance with an embodiment of the disclosure.

In practice, the reference pattern 88 provides known reference points for spatial registration with images of adjacent portions of the scanned dental arch 120. Thus, referring to FIG. 12, when an optical scanner 10 is employed to scan the dental arch 120, it simultaneously scans at least an adjacent portion of the reference pattern 88, thereby capturing an image of the reference pattern with the image of the dental arch (or the portion thereof) that has been scanned. Thus, at least a portion of the tooth geometry in the dental arch 120 is captured in the scan image along with at least a portion of the reference pattern 88. The combined dental arch/reference pattern image is digitized by, for example, an A/D converter 170 (which may be a component of the scanner 10 or a separate component) and input into a processor 172. The processor 172 also receives input from an input device 174 (keyboard, mouse, touch screen, etc.) through which the position settings (as determined, for example from the numbered detents in the first, second, and third adjustment rods, as described above) of the first, second and third reference pattern adjustment mechanisms are entered manually by an operator. Also entered are values for the positions of the nasion relator adjustment mechanism and the nasion pad stabilizer arm 62, which are determined from the numbered detents associated with these components, as described above. The operator may also enter, via the input device 174, other data, such as patient identification data, a scanning date and time, and a treatment stage number.

The processor is programmed to create a digital input data set from the operator-entered inputs, and then to match the digital input data set with an image data set that includes the digitized images of the scanned dental arch 120 and the reference pattern 88 in registration with each other. The result is a combined data file that may be stored in a memory device 176 operatively associated with the processor 172. The combined data file thus includes data representing a scanned dental arch image in registration with the reference pattern 88, so that any image of a part of the dental arch may be located and oriented properly, via registration with the reference pattern 88, with respect to an image of any other part of the dental arch. The combined data file also includes all of the position settings used to obtain each scanned image. The processor 172 may output the data in the combined data file to an output device 178, such as a monitor or a printer that presents the scanned image and the other data in a useful visual format.

Because the position settings are all discrete values representing the detented positions of the various adjustment mechanisms, they are easily entered, and they are easily reproduced at a later time for taking a subsequent scan of the dental arch of the same patient. For example, once the position settings for a patient are known, the same settings will be used for all subsequent scans of that patient. This facilitates the comparison of any scan of that patient with any previous scan to ascertain, for example, the progress of a course of orthodontic or prosthodontic treatment. Such a comparison may be made visually, for example, by outputting the scanned images to the output device 178 for visual inspection, or the comparison may be made computationally by the processor 172, with the computed comparison results being represented graphically or numerically by the output device 178.

For example, a scan of a patient's dental arch at T1 is taken with the dentition in registration with the reference pattern, and with a set of reproducible position settings for the position adjustment mechanisms of the head brace. A scan of the same dental arch at a later time T2, taken with the dentition in registration with the same reference pattern and with the same position settings, enables any changes in the dentition geometry to be easily observable and quantifiable, thereby allowing the progress of the patient's treatment to be readily determined, so that the need for changes in the course of treatment may be quickly ascertained.

Thus, the ability to make easy and accurate comparisons of the dental arch of a patient at two different times, representing, for example, two stages of treatment, provides accuracy in registering, in three dimensions, the changes that have occurred in the patient's dentition geometry between a scan taken at first time T1 and a scan taken at a subsequent time T2. As a result, the dentition geometry of a patient can be registered at T1 and then at T2 to observe changes that have occurred in the interval between T1 and T2, without the need to use X-rays or radiographs for each measurement, with a "stable" landmark superimposed in the X-rays.

Figure 13:
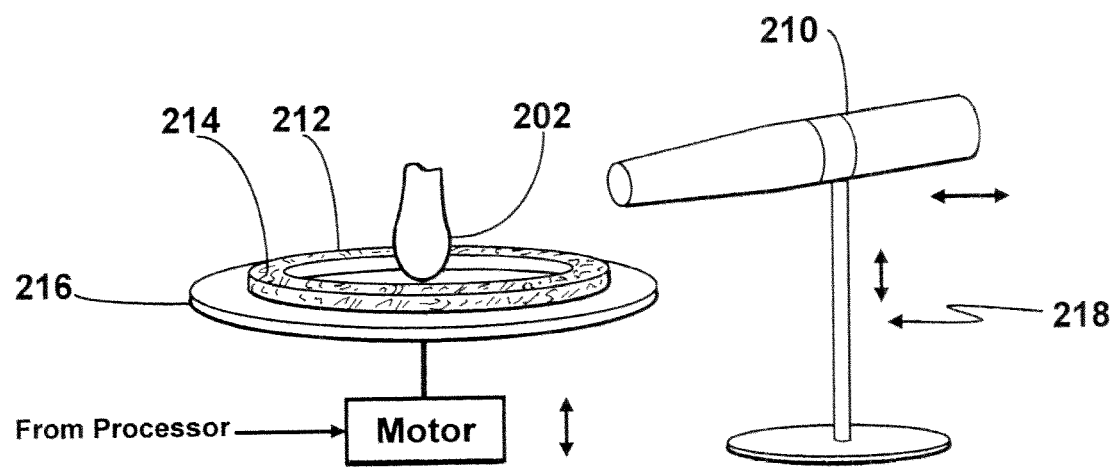
FIG. 13 is a semi-schematic representation of a scanning system in accordance with another embodiment of the disclosure.

The concept of this disclosure may be applied in other applications, such as, for example, the scanning of objects that have relatively large areas without distinctive surface figures. An embodiment of a scanning system 200 in accordance with this disclosure that may be employed in such applications is illustrated in FIG. 13. In this embodiment, an object 202 to be scanned by a scanner 210 (e.g., an optical scanner) is held in a fixed location relative to a reference element 212 having a reference pattern 214 thereon. Preferably, the reference pattern 214 is three-dimensional, but a two-dimensional reference pattern may be adequate or suitable in certain applications. The object 202 and the reference element 212 are scanned simultaneously to obtain a scanned image of a first portion of the object 202 in registration with the reference pattern 214. The position of the object 202 and the reference element 212 relative to the scanner is then adjusted, and object 202 and the reference element 212 are again scanned to obtain a scanned image of a second portion of the object 202 in registration with the reference pattern 214. These steps are repeated until a set of images of the entire object 202 in registration with the reference pattern 214 is obtained. This set of images may be digitized and input to a processor (such as the processor 172 of FIG. 12), which is programmed to "stitch" the images together to produce a unified image of the entire object 202, either with or without the reference pattern 214 shown in registration.

The relative position of the object 202 and the reference element 212 to the scanner may be adjusted either by moving the object and the reference element sequentially from a first position to a second position to a third position, etc., with the scanner remaining stationary, or by fixing the object and reference element in one location and moving the scanner sequentially through the several positions. One exemplary mechanism for carrying out the former method may include, as a fixation device, a movable platform 216 (such as, for example, a turntable) on which the object 202 and the reference element 212 are fixed. The platform 216 may be rotatable through a sequence of rotational positions relative to the scanner 210, and, optionally, it may be vertically adjustable relative to the scanner. The movement of the platform 216 may be under the control of a processor (such as the processor 172 of FIG. 12) to be moved through a sequence of discrete rotational (and, optionally, vertical) positions, at each of which the motion of the platform 216 is stopped so that the object 202 and the reference element 212 may be scanned. An exemplary mechanism for moving the scanner 210, while maintaining the object 202 and the reference element 212 in a fixed position, may include a scanner fixture 218 to which the scanner 210 (or, more properly, the scanning head of the scanner) is mounted. The fixture 218 is operable to allow the scanning head to be moved vertically, horizontally, and/or rotationally through a sequence of discrete scanning positions (again, for example, under the control of the processor 172) with respect to the object 202 and the reference element 212. At each of the scanning positions, the motion of the fixture 218 is halted so that the object and the reference element can be scanned.

The description of several embodiments in this disclosure is in no way limiting. The described embodiments are exemplary only, and it is understood that several modifications and variations may suggest themselves to those of ordinary skill in the art, and should be considered to be within the spirit and scope of this disclosure.

What is claimed is:

1. A method for tracking progress of a patient undergoing orthodontic treatment, the method comprising:
    providing a physical reference device for positioning proximate to a dental arch of the patient;
    generating, via one or more processors, a three-dimensional (3D) model of the dental arch of the patient while the patient is undergoing the orthodontic treatment, wherein the 3D model is generated by:
        receiving a plurality of images of the dental arch that are obtained while the physical reference device is positioned proximate to the dental arch, wherein at least some images of the plurality of images include a portion of the dental arch together with a portion of the physical reference device,
        for each image of the at least some images including the portion of the dental arch together with the portion of the physical reference device, determining a registration location and a registration orientation between the each image and at least one other image of the at least some images using the portions of the physical reference device in the respective images to improve registration accuracy, and
        stitching the at least some images together according to the determined registration locations and registration orientations to generate at least a portion of the 3D model of the dental arch; and
    outputting, via the one or more processors, data associated with a comparison of the 3D model of the dental arch to a previous 3D model representing an earlier state of the dental arch for assessing progress of the orthodontic treatment, wherein the previous 3D model is generated using the physical reference device.

2. The method of claim 1, wherein the orthodontic treatment comprises providing a series of appliances to the patient.

3. The method of claim 1, wherein assessing the progress of the orthodontic treatment comprises comparing positions of teeth in the 3D model to positions of the teeth in the previous 3D model.

4. The method of claim 1, wherein the previous 3D model represents the dental arch at an earlier stage of the orthodontic treatment.

5. The method of claim 1, wherein the previous 3D model represents the dental arch before the patient started the orthodontic treatment.

6. The method of claim 1, wherein the data comprises a graphical representation of the comparison of the 3D model to the previous 3D model.

7. The method of claim 1, wherein the data comprises a numerical representation of the comparison of the 3D model to the previous 3D model.

8. The method of claim 1, wherein determining the registration location and the registration orientation between the each image and the at least one other image comprises using the portions of the physical reference device in the respective images to determine a location and an orientation of the each image with respect to the at least one other image.

9. The method of claim 1, wherein determining the registration location and the registration orientation between the each image and the at least one other image comprises:
    identifying one or more reference points on the portions of the physical reference device in the respective images; and
    using the one or more reference points to register the each image to the at least one other image.

10. The method of claim 1, wherein the physical reference device includes a reference pattern on a surface thereof, and wherein the each image and the at least one other image are registered to each other based on the reference pattern.

11. The method of claim 10, wherein the reference pattern is a two-dimensional (2D) pattern.

12. The method of claim 10, wherein the reference pattern is a 3D pattern.

13. The method of claim 1, wherein the plurality of images are generated by an optical scanner.

14. The method of claim 13, wherein the optical scanner is an intraoral scanner.

15. The method of claim 1, wherein the 3D model depicts the entirety of the dental arch.

16. The method of claim 1, wherein the dental arch is a lower dental arch of the patient, the 3D model is a first 3D model, and the method further comprises:
    generating a second 3D model of an upper dental arch of the patient while the patient is undergoing the orthodontic treatment, wherein the second 3D model is generated by:
        receiving a plurality of second images of the upper dental arch, at least some second images of the plurality of second images including a portion of the upper dental arch together with a portion of the physical reference device, for each second image of the at least some second images including the portion of the upper dental arch together with the portion of the physical reference device, determining a registration location and registration orientation between the each second image and at least one other second image using the portions of the physical reference device in the respective second images to improve registration accuracy, and stitching the at least some second images together according to the determined registrations locations and registration orientations to generate at least a portion of the second 3D model of the upper dental arch; and outputting, via the one or more processors, data associated with a comparison of the second 3D model of the upper dental arch to a second previous 3D model representing an earlier state of the upper dental arch for assessing the progress of the orthodontic treatment, wherein the second previous 3D model is generated using the physical reference device.

17. The method of claim 1, wherein the physical reference device is in a fixed position relative to the dental arch.

18. The method of claim 17, wherein the physical reference device is coupled to the patient in the fixed position by a fixation device.

19. The method of claim 1, wherein the physical reference device is spaced apart from an occlusal surface of the dental arch.

20. The method of claim 1, further comprising:
receiving an input data set including one or more of the following: patient identification data, scan date, scan time, or treatment stage; and
associating the input data set with the 3D model.

21. A method for tracking progress of a patient undergoing orthodontic treatment, the method comprising:

providing a physical reference device for positioning proximate to a dental arch of the patient;

generating, via one or more processors, a three-dimensional (3D) model of a dental arch of the patient while the patient is undergoing the orthodontic treatment, wherein the 3D model is generated by:
positioning the physical reference device proximate to the dental arch,
obtaining a plurality of images of the dental arch while the physical reference device is positioned proximate to the dental arch, wherein at least some images of the plurality of images include a portion of the dental arch together with a portion of the physical reference device,
for each image of the at least some images including the portion of the dental arch together with the portion of the physical reference device, determining a registration location and a registration orientation between the each image and at least one other image of the at least some images using the portions of the physical reference device in the respective images to improve registration accuracy, and
stitching the at least some images together according to the determined registrations locations and registration orientations to generate at least a portion of the 3D model of the dental arch;

comparing, via the one or more processors, the 3D model of the dental arch to a previous 3D model representing an earlier state of the dental arch, wherein the previous 3D model is generated using the physical reference device; and outputting, via the one or more processors, data indicative of the comparison of the 3D model of the dental arch to the previous 3D model.

* * * * *

UNITED STATES PATENT AND TRADEMARK OFFICE
CERTIFICATE OF CORRECTION

PATENT NO. : 12,383,382 B2
APPLICATION NO. : 17/444037
DATED : August 12, 2025
INVENTOR(S) : Eric Kuo Page 1 of 1

It is certified that error appears in the above-identified patent and that said Letters Patent is hereby corrected as shown below:

In the Claims

In Column 13, in Claim 16, Line 11, delete "registrations" and insert -- registration --, therefor.

In Column 14, in Claim 21, Line 24, delete "registrations" and insert -- registration --, therefor.

Signed and Sealed this
Sixteenth Day of September, 2025

Coke Morgan Stewart
*Acting Director of the United States Patent and Trademark Office*